(12) United States Patent
Takamatsu et al.

(10) Patent No.: US 6,579,976 B2
(45) Date of Patent: *Jun. 17, 2003

(54) PROCESS FOR PRODUCING 2',3'-DIETHYL SUBSTITUTED NUCLEOSIDE DERIVATIVES

(75) Inventors: Satoshi Takamatsu, Kawasaki (JP);
Satoshi Katayama, Kawasaki (JP);
Naoko Hirose, Kawasaki (JP);
Kunisuke Izawa, Kawasaki (JP)

(73) Assignee: Ajinomoto Co., Inc., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/427,082

(22) Filed: Oct. 26, 1999

(65) Prior Publication Data

US 2002/0045744 A1 Apr. 18, 2002

(30) Foreign Application Priority Data

Nov. 2, 1998 (JP) ............................................ 10-311918

(51) Int. Cl.$^7$ ........................ C07H 19/173; C07H 19/06
(52) U.S. Cl. .................. 536/27.6; 536/27.8; 536/27.81; 536/28.5; 536/28.53; 536/28.54; 536/27.4; 536/27.11; 536/27.12; 536/27.14; 536/28.1; 536/28.4; 536/28.51; 536/28.52
(58) Field of Search .......................... 536/27.11, 27.4, 536/27.8, 27.14, 27.6, 27.12, 28.4, 28.1, 28.5, 28.51, 28.52, 28.53, 28.54, 28.55

(56) References Cited

U.S. PATENT DOCUMENTS

| | | | | |
|---|---|---|---|---|
| 4,900,407 | A | * | 2/1990 | Saito et al. |
| 5,137,876 | A | * | 8/1992 | MacGoss et al. |
| 5,290,927 | A | | 3/1994 | Honda et al. |
| 5,310,895 | A | | 5/1994 | Shiragami et al. |
| 5,466,793 | A | | 11/1995 | Honda et al. |
| 5,625,057 | A | * | 4/1997 | Shiragami et al. |
| 5,633,366 | A | * | 5/1997 | Takamatsu et al. |
| 6,090,937 | A | * | 7/2000 | Takamatsu et al. |
| 6,245,910 | B1 | * | 6/2001 | Izawa et al. |

FOREIGN PATENT DOCUMENTS

RU   2108339   9/1994

OTHER PUBLICATIONS

Barton et al., J. Org Chem., vol. 58, No. 24, 6838–3842, 1993.*
D.H.R. Barton, et al., Journal of Organic Chemistry, vol. 58, No. 24, pp. 6838–6842, "The Invention of Radical Reactions. 32. Radical Deoxygenations, Dehalogenations, and Deaminations With Dialkyl Phosphites and Hypophosphorous Acid as Hydroogen Sources", Nov. 19, 1993.
D.H.R. Barton, et al., Tetrahedron Letters, vol. 33, No. 39, pp. 5709–5712, "Hypophosphorous Acid and its Salts: New Regents for Radical Chain Deoxygenation, Dehalogenation and Deamination", Sep. 22, 1992.

* cited by examiner

Primary Examiner—James O. Wilson
Assistant Examiner—Patrick Lewis
(74) Attorney, Agent, or Firm—Oblon, Spivak, McClelland, Maier & Neustadt, P.C.

(57) ABSTRACT

There can be provided an excellent industrial process for producing compounds having sugar-moiety hydroxyl groups or halogen atoms reduced in nucleic acids or in derivatives thereof by allowing O-thiocarbonyl derivatives of sugar-moiety hydroxyl groups or allowing halogenated derivatives in the sugar-moiety, in the nucleic acids or in derivatives thereof to react with any one of hypophosphorous acids (including salts thereof) and phosphites (esters) which are inexpensive, non-toxic and safely usable as radical reducing agents in industrial scale, in the presence of a radical reaction initiator.

The process of the present invention is an industrially useful and highly safe process for reducing sugar-moiety hydroxyl groups and halogen atoms in nucleic acids or derivatives thereof (including nucleic acid-related compounds) at low costs.

20 Claims, No Drawings

PROCESS FOR PRODUCING 2',3'-DIETHYL SUBSTITUTED NUCLEOSIDE DERIVATIVES

BACKGROUND OF THE INVENTION

1. Field of the Invention

The present invention relates to a novel process for producing nucleic acid derivatives and in particular to an industrially useful process for reducing sugar-moiety hydroxyl groups and halogen atoms in nucleic acids and their derivatives (their related compounds etc.).

According to the present invention, an intermediate for producing various pharmaceutical preparations, for example an intermediate for producing 9-(2,3-dideoxy-2-fluoro-β-D-threo-pentofuranosyl) adenine (also may be called "FddA" as the abbreviation in the specification) and 2',3'-dideoxyadenosine (also may be called "ddA" as the abbreviation in the specification) useful as antiviral agents can be produced industrially advantageously.

2. Description of the Related Art

For dehydroxylation (deoxylation) of sugar-moiety hydroxyl groups in nucleic acids or in their related compounds, the method of radically reducing thiocarbonyl derivatives of such hydroxyl groups has been generally used. Further, for dehalogenation of sugar-moiety halogen atoms in nucleic acids or in their related compounds, the method of radically reducing them has been generally used (for example, see A. G. Sutherland, "Comprehensive Organic Functional Group Transformations", Vol. 1, A. R. Katritzky, et al., Ed., Pergamon, London, pp. 1–25).

In the radical reduction described above, tin compounds such as tributyl tin hydride are used most generally as radical reducing agents. However, tin compounds when used in industrial production are problematic in their toxicity during operation, and when used in production of pharmaceutical preparations etc., their presence even in a trace amount is not allowable and their use is virtually not possible. Silyl hydride-type compounds such as tris (trimethylsilyl) silane are used as radical reducing agents in some cases, but these silyl hydride-type compounds are generally not produced in industrial scale, and even if produced, they are very expensive and very difficult to use in industry.

In recent years, Barton et al. conducted radical reduction of thiocarbonyl derivatives and halogen atoms with hypophosphorous acid or salts thereof or with esters of phosphorous acid (for example, see D. H. R. Barton, et al., Tetrahedron Lett., 33(39), 5709 (1992) and D. H. R. Barton, et al., J. Org. Chem., 58, 6838 (1993)). However, these literatures illustrate the radical reduction of only simple hydrocarbons or sugar derivatives having a few functional groups, and whether this radical reduction can be applied to complex heterocyclic nucleic acid derivatives was not known.

Accordingly, there is a need for an industrially advantageous and safe process applicable widely to nucleic acid derivatives in order to produce the reduced compound.

PROBLEMS TO BE SOLVED BY THE INVENTION

The object of the present invention is to establish an industrially useful and highly safe process for producing the reduced compounds at low costs, wherein sugar-moiety hydroxyl groups and halogen atoms in nucleic acids or in their derivatives (including their related compounds etc.) can be selectively reduced to advantageously produce a wide variety of useful nucleic acid derivatives such as intermediates for producing the active ingredients (FddA, ddA etc.) in pharmaceutical preparations.

SUMMARY OF THE INVENTION

As a result of their eager study to solve the problem described above, the present inventors found that compounds wherein sugar-moiety hydroxyl groups or halogen atoms in nucleic acids and derivatives thereof (referred to collectively as "nucleic acid derivatives") have been reduced can be easily obtained by allowing O-thiocarbonyl derivatives of sugar-moiety hydroxyl groups, or halogenated derivatives in the sugar-moiety thereof, to react with any one of hypophosphorous acids (including salts thereof) and esters of phosphorous acid which are inexpensive, non-toxic and safely usable as radical reducing agents in industrial scale, in the presence of a radical reaction initiator, and as a result, the present inventors found that it is thereby possible to derive a wide variety of useful nucleic acid derivatives industrially efficiently, to arrive at the completion of the present invention.

That is, the present invention encompasses the following inventions.

(i) A process for producing a nucleic acid derivative represented by the general formula (II):

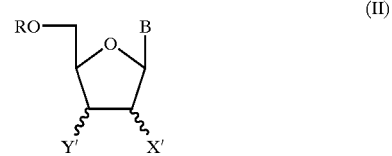

wherein B represents a nucleic acid base, R represents a hydrogen atom or a hydroxy group-protecting group, and one of Y' and X' represents a hydrogen atom and the other represents a hydrogen atom, a fluorine atom, a hydroxyl group or a protected hydroxyl group, respectively, which comprises allowing a nucleic acid derivative having an eliminating group represented by the general formula (I):

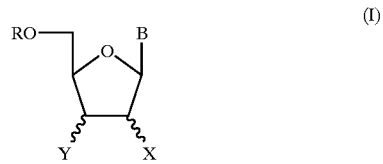

wherein B and R have the same meanings as defined above, and one of Y and X represents an eliminating group and the other represents a hydrogen atom, a fluorine atom, a hydroxyl group or a protected hydroxyl group, respectively, to react with at least one compound selected from hypophosphorous acid (including salts thereof) and esters of phosphorous acid in the presence of a radical reaction initiator. In this reaction, the above eliminating group is reduced and converted into a hydrogen atom.

In the present invention, the nucleic acid base represented by the above group B also includes nucleic acid base derivatives. The nucleic acid base derivatives include e.g. N-acetylguanine, N-acetyladenine, N-benzoylguanine, N-benzoyladenine, 2-amino-6-chloropurine and 6-chloropurine.

(ii) The process according to item (i) above, wherein B is a purine base or a pyrimidine base or a derivative thereof.

(iii) The process according to any one of the above items, wherein B is any one of hypoxanthine, adenine, guanine, uracil, thymine and cytosine, or a derivative thereof.

(iv) The process according to item (i) above, wherein R is any one of a hydrogen atom, an acyl group, an alkyl group, an aralkyl group and a silyl group.

(v) The process according to any one of the above items, wherein R is any one of a hydrogen atom, an acetyl group, a benzoyl group and a trityl group.

(vi) The process according to any one of the above items, wherein the eliminating group is either a halogen atom excluding a fluorine atom or an O-thiocarbonyl derivative (residue).

The halogen atom includes the respective atoms of chlorine, bromine and iodine, and the O-thiocarbonyl derivative (residue) includes O-phenoxythiocarbonyl group: PhO(C=S)O—, O-parafluorophenoxythiocarbonyl group: p-F—PhO(C=S)O—, O-methylthiothiocarbonyl group: MeS(C=S)O—, O-phenylthiothiocarbonyl group: PhS(C=S)O—, and O-imidazolylthiocarbonyl group:

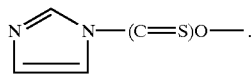

(vii) The process according to any one of the above items, wherein one of Y and X is an eliminating group and the other is any one of a hydroxyl group, an acyloxy group, an alkyloxy group, an aralkyloxy group and a silyloxy group.

(viii) The process according to any one of the above items, wherein one of Y and X is an eliminating group and the other is any one of a hydroxyl group, an acetyloxy group and a benzoyloxy group.

(ix) The process according to any one of the above items, wherein hypophosphorous acid is in the form of sodium hypophosphite.

(x) The process according to item (i) above, wherein the radical reaction initiator is an azo compound.

The azo compound is preferably an azonitrile compound, an azoamidine compound, a cyclic azoamidine compound, an azoamide compound, an alkyl azo compound etc. Specific individual compounds contained in these respective compounds include compounds known to be contained in these compounds, but may be compounds to be found in the future.

(xi) The process according to any one of the above items, wherein the compound produced in the above process wherein B is a purine base or a derivative thereof, Y' is a hydrogen atom, X' is a hydroxyl group or a protected hydroxyl group, is subjected to at least one step selected from the step deprotecting the hydroxyl group, the step of halogenation at the 6-position, the step of amination at the 6-position and the step of fluorination at the 2'-position to produce FddA.

(xii) A process for producing a derivative substituted with a halogen at the 6-position, wherein the nucleic acid derivative of the general formula (II) obtained above wherein B is 6-hydroxypurine is halogenated selectively at the 6-position with a halogenating agent for example a chlorinating agent of a combination of phosphorus oxychloride and N,N-dimethylaniline or sulfuryl chloride and dimethylformamide or a chlorinating agent such as dimethyl chloromethylene ammonium chloride and if necessary the product is subjected to the step of deprotection, to produce the derivative halogenated at the 6-position.

(xiii) A process for producing FddA, wherein the derivative halogenated at the 6-position obtained above is further subjected to a method of replacing the halogen atom by an amino group (ammonia treatment etc.) and a method of substituting the 2-position with fluorine (treatment with diethylaminosulfur trifluoride, morpholinosulfur trifluoride, or etc.) in this order or in the reverse order and as necessary the product is subjected to the step of deprotection to produce FddA.

(xiv) A process for producing ddA, wherein the nucleic acid derivative of the general formula (II) obtained above wherein B is adenine and Y' and X' are hydrogen atoms is subjected to the step of deprotecting the hydroxyl group with an acid or an alkali as necessary to produce ddA.

DETAILED DESCRIPTION OF THE INVENTION

In the nucleic acid derivatives having an eliminating group, represented by the general formula (I) and used as the starting material in the present invention, B represents nucleic acid bases such as purine base and pyrimidine base (including various derivatives thereof). Specifically, the pyrimidine base preferably includes uracil, thymine, cytosine etc. and the purine base preferably includes hypoxanthine, adenine, guanine etc. Further, hydroxyl groups, amino groups etc. in these nucleic acid bases may have been protected with protecting groups generally used in synthesis of nucleic acid, for example with acyl groups such as acetyl and benzoyl or aralkyl groups such as benzyl and triphenyl methyl group. Further, as described above, the nucleic acid bases also include various derivatives thereof (e.g. derivatives substituted with halogen atom(s)).

In the general formula (I) above, R represents a hydrogen atom or a hydroxy group-protecting group. The hydroxy group-protecting group is preferably a protecting group which may have a substituent group (halogen atom, $C_1$ to $C_5$ alkyl group, $C_1$ to $C_5$ alkyloxy group etc.), for example an acyl group such as acetyl or benzoyl, an alkyl group such as methoxymethyl or allyl, an aralkyl group such as benzyl or triphenyl methyl, and a silyl group such as trimethyl silyl, and a protecting reagent therefor is preferably an acylating agent, an alkylating agent, an aralkylating agent and an organic silylating agent.

If Y is a protected hydroxyl group, R may be combined with Y to form a protecting group. Examples of protecting groups formed by combining R with Y include cyclic protecting groups which may have substituent groups (halogen atom, $C_1$ to $C_5$ alkyl group, $C_1$ to $C_5$ alkyloxy group etc.), preferably cyclic acetal groups and cyclic ketal groups such as ethylidene, isopropylidene and benzylidene, cyclic silyl groups such as di-t-butylsilylene, 1,1,3,3-tetraisopropyldisiloxanilidene, tetra-t-butoxydisiloxane-1,3-diylidene, etc.

One of X and Y represents an eliminating group and the other represents any one of a hydrogen atom, a fluorine atom, a hydroxyl group and a protected hydroxyl group. Here, the eliminating group represents groups to be eliminated upon radical reaction, particularly groups or atoms to be replaced by hydrogen atoms upon radical reduction reaction, and preferable examples include halogen atoms (chlorine atom, bromine atom, iodine atom) excluding a fluorine atom, as well as O-thiocarbonyl derivatives (residues) represented by the general formula (III):

In the compounds represented by the general formula (III) above, Z represents any one of H, NR'R", OR' and SR', and R' and R" are independent of each other and each represent any substituent group of aryl groups (phenyl, tolyl, naphthyl etc.), alkyl groups ($C_1$ to $C_5$) or aralkyl groups (benzyl, phenethyl etc. ) and alkyloxy groups ($C_1$ to $C_5$) and alkylamino groups (methylamino, ethylamino, dimethylamino etc.) which may have substituent groups (halogen atom etc.), respectively. R' and R" may be the same or different or may be combined to form a single cyclic group. Examples of single cyclic groups formed by their combination include cyclic ethers ($C_1$ to $C_5$), cyclic amines ($C_1$ to $C_5$) etc.

Preferable examples of the above group Z include a hydrogen atom, methyl group, phenyl group, 1-imidazole group, N-morpholino group, methyloxy group, phenyloxy group, parafluorophenyloxy group, methylthio group, phenylthio group etc.

In the above general formula (I), the halogen atoms (excluding a fluorine atom) in the eliminating group include e.g. a chlorine atom, a bromine atom and an iodine atom.

In the compounds represented by the above general formula (I), the O-thiocarbonyl derivative in the eliminating group preferably includes an O-thioformyl group: $H(C=S)O-$, O-methylthiocarbonyl group, O-phenylthiocarbonyl group, O-(1-imidazole) thiocarbonyl group, O—(N-morpholino) thiocarbonyl group:

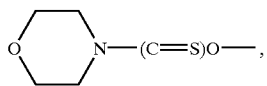

O-methoxythiocarbonyl group: $MeO(C=S)O-$, O-phenoxythiocarbonyl group, O-parafluorophenoxythiocarbonyl group, O-methylthiothiocarbonyl group, O-phenylthiothiocarbonyl group etc.

In the compounds of the above general formula (I), the protected hydroxyl group represented by X or Y preferably includes acyloxy groups such as acetyloxy and benzoyloxy, alkyloxy groups such as methoxymethyloxy and allyloxy, aralkyloxy groups such as benzyloxy and triphenylmethyloxy, and silyloxy groups such as trimethylsilyloxy, and these may have substituent groups (halogen atom, $C_1$ to $C_5$ alkyl group, $C_1$ to $C_5$ alkyloxy group etc.).

X and Y in the above general formula (I) showing the compounds used as the starting material in the present invention may maintain the stereostructure of either α- or β-configuration, and these configurations are specifically shown inthe general formulae (IV) to (VII) described below. However, it is evident that the compounds wherein R is a hydrogen atom and X or Y is an eliminating group have the stereostructure of either α- or β-configuration.

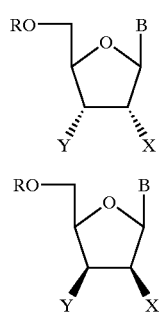

(IV)

(V)

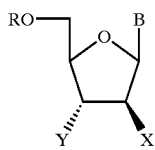

(VI)

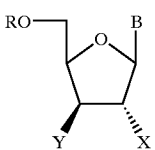

(VII)

In the above formulae, B represents a nucleic acid base, R represents a hydrogen atom or a hydroxy group-protecting group, and one of Y and X represents an eliminating group and the other represents a hydrogen atom, a fluorine atom, a hydroxyl group or a protected hydroxyl group.

Further, the compounds represented by the above general formula (II) obtained by the process of the present invention are compounds wherein the eliminating group in the above general formula (I) is reduced to form a hydrogen atom, so if the other group than the reduced group is a fluorine group, a hydroxyl group or a protected hydroxyl group, the compounds maintain the stereostructure at the respective positions and/or the stereostructure of either α- or β-configuration. Specifically, the compounds are shown in any of the following general formulae (VIII) to (XI):

(VIII)

(IX)

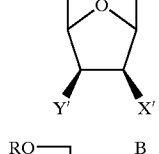

(X)

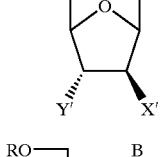

(XI)

In the above formulae, B and R have the same meanings as defined above, and one of Y' and X' represents a hydrogen atom and the other represents a hydrogen atom, a fluorine atom, a hydroxyl group or a protected hydroxyl group.

These nucleic acid derivatives having an eliminating group represented by the above general formula (I) wherein the eliminating group is a halogen atom excluding a fluorine atom can be synthesized arbitrarily by any methods generally used for synthesis of nucleic acid derivatives (for example, see T. Ueda, "Chemistry of Nucleosides and Nucleotides", Vol. 1, L. B. Townsend, Ed., Plenum Press, New York (1988), pp. 76–79 and P. C. Srivastava, et al., "Chemistry of Nucleosides and Nucleotides", Vol. 1, L. B. Townsend, Ed., Plenum Press, New York (1988), pp. 181–189).

For example, derivatives such as 9-(2,5-di-O-acetyl-3-bromo-3-deoxy-β-D-xylofuranosyl) adenine and 9-(2,5-di-O-acetyl-3-bromo-3-deoxy-β-D-xylofuranosyl) hypoxanthine can be easily produced according to a known method (for example, see Shiragami et al., Nucleosides & Nucleotides, Vol. 15(1–3), p. 31 (1996)).

As described in the literature, an acid halide (acetyl bromide, acetyl chloride etc.) is allowed to act on a nucleic acid derivative having a hydroxyl group whereby a desired halogen atom can be introduced into it.

In addition, these nucleic acid derivatives having an eliminating group represented by the above general formula (I) wherein the eliminating group is an O-thiocarbonyl derivative (residue) can be arbitrarily synthesized by introducing a thiocarbonyl group to the corresponding nucleic acid derivatives having a hydroxyl group. The corresponding nucleic acid derivatives having a hydroxyl group can be arbitrarily synthesized by any methods generally used for synthesis of nucleic acid derivatives (for example, the method described in "Chemistry of Nucleosides and Nucleotides", L. B. Townsend, Ed., Plenum Press, New York (1988)).

To introduce the thiocarbonyl group, a generally used method (for example, see S. W. McCombie "Comprehensive Organic Synthesis", Vol. 8, B. M. Trost, Ed., Pergamon Press (1991), pp. 818–824) can be used. The desired compounds can be obtained by allowing the corresponding nucleic acid derivatives having a hydroxyl group to react with thiocarbonyl halides represented by the general formula (XII) below or to react with carbon disulfide and alkyl halides corresponding to R' when Z is SR'.

(XII)

In the above formula, Z represents any one of H, NR'R", OR' and SR', and R' and R" may be independent of each other and each represent any substituent group of an aryl, alkyl or aralkyl group and alkyloxy and alkylamino groups which may have a substituent group (halogen atom etc.), respectively. R' and R" may be the same or different or may be combined to form a single cyclic group. Examples of single cyclic groups formed by their combination include cyclic ethers ($C_1$ to $C_5$), cyclic amines ($C_1$ to $C_5$) etc., and specific examples include an imidazole group, a morpholino group etc. "A" represents a halogen atom.

The reaction of introducing the thiocarbonyl group may be conducted in the presence of an equivalent-range base. The reaction may be conducted in a suitable solvent, and preferably, the suitable solvent includes organic solvents such as ethyl acetate, toluene, methylene chloride, acetonitrile and a mixed solvent thereof. The reaction in this case can be conducted at −80° C. to the reflux temperature of the solvent. After the reaction, the base is neutralized if necessary and the reaction mixture is subjected in a usual manner to extraction with an organic solvent such as ethyl acetate, toluene and methylene chloride whereby the thiocarbonyl derivative can be isolated. After the reaction, the reaction mixture can be used directly in radical reduction reaction without isolating the thiocarbonyl derivative.

In the present invention, any one of hypophosphorous acid, salts of hypophosphorous acid and esters of phosphorous acid is used as a radical reducing agent. Preferable examples of salts of hypophosphorous acid include alkali metal salts such as sodium hypophosphite, alkaline earth metal salts such as calcium hypophosphite, amine salts such as ammonium hypophosphite, and metal salts such as nickel hypophosphite and (II).

Preferable examples of such esters of phosphorous acid include lower alcohol ($C_1$ to $C_5$) phosphorous acid ester (mono-, di-ester), such as dimethyl phosphite, diethyl phosphite etc.

The radical reaction initiator used in the present invention may be any of those known as radical reaction initiators and radical reaction reagents, and such radical reaction initiators may be preferably azo compounds. Preferable examples of azo compounds include azonitrile compounds such as azobisisobutyronitrile, azoamidine compounds such as 2,2'-azobis(2-methylpropionamidine) dihydrochloride (trade name: V-50), cyclic azoamidine compounds such as 2,2'-azobis [2-(2-imidazoline-2-yl) propane] dihydrochloride (trade name: VA-044), 2,2'-azobis[2-(2-imidazoline-2-yl) propane] disulfate (trade name: VA-044B) and 2,2'-azobis [2-(2-imidazoline-2-yl) propane] (trade name: VA-061), azoamide compounds such as 2,2'-azobis[2-methyl-N-(2-hydroxyethyl) propionamide] (trade name: VA-086), and alkyl azo compounds such as azodi-t-octane (trade name: VR-110).

The radical reduction reaction can be conducted using an equivalent to excess radical reaction reagent in a solvent preferably water, but may be conducted in an organic solvent such as ethyl acetate, toluene, methylene chloride and acetonitrile (or a mixture of these solvents). The reaction may also be conducted in an arbitrary mixture of water and one or more of these organic solvents as the solvent. The reaction may be conducted at room temperature to the reflux temperature of the solvent. An equivalent or more radical reaction initiator can be used, but usually a catalytic amount (0.1 to 100 mol-%) suffices. After the reaction, the product is isolated by extracting the reaction mixture with an organic solvent such as ethyl acetate, toluene or methylene chloride in a usual manner, or by merely filtering its formed crystals.

Out of the compounds of the above general formula (II) obtained in the manner as described above, the compound wherein B is adenine, Y' is a hydrogen atom, X' is a hydrogen atom or a fluorine atom in the β-configuration and R is a hydrogen atom, is used as a pharmaceutical preparation or it is an expected compound 2',3'-dideoxyadenosine (ddA) or 9-(2,3-dideoxy-2-fluoro-β-D-threopentofuranosyl) adenine (FddA), or the product wherein R is not a hydrogen atom but a protecting group can be subjected to a deprotection step to be easily converted into the above ddA or FddA. In this case, the protecting group R for the hydroxyl group at the 5'-position is eliminated in a usual manner with acid or alkali as necessary whereby the objective compound can be produced.

For example, if the protecting group R for the hydroxyl group at the 5'-position is a trityl group which may have a substituent group, the compounds are treated with an acid such as acetic acid so that they can be deprotected.

In the above, the compounds wherein B is not adenine but 6-halogenopurine are subjected in a usual manner to the step of amination at the 6-position whereby an amino group is introduced into the 6-position thereof, and in the case of those wherein R is not a hydrogen atom but a hydroxy group-protecting group, the objective protecting group is similarly eliminated (deprotected) before or after the step of amination at the 6-position whereby ddA or FddA can be produced. If X' is neither a hydrogen atom nor a fluorine atom at the β-configuration but a hydroxyl group (protected or not protected), the hydroxyl group is dehydroxylated in a usual manner, or dehydroxylated and fluorinated at the β-position, whereby ddA or FddA can be produced. In this case, the step of dehydroxylating the hydroxyl group or the step of dehydroxylation-fluorination at the β-position can be conducted using any methods known in the art.

If B is not adenine (if B is adenine, ddA and FddA can be produced by the step of dehydroxylation or dehydroxylation-fluorination at the β-position and subsequent deprotection of R as necessary when R is a protecting group) but 6-halogenopurine, then the dehydroxylation step or the dehydroxylation-fluorination at the β-position can also be conducted before the step of amination at the 6-position.

Similarly, the compound (II) produced in the present invention wherein B is 6-hydroxypurine, Y' is a hydrogen atom and X' is a hydroxyl group or a protected hydroxyl group is subjected to the step of halogenation at the 6-position to produce the compound substituted with a halogen at the 6-position, which is then subjected to the step of fluorination at the 2'-β-position and the step of amination at the 6-position, and if R is a protecting group, the compound is further subjected to the step of deprotection whereby FddA can be produced.

However, the order of the step of fluorination at the 2'-β position and the step of amination at the 6-position is particularly not limited. Further, if the compound has a protected hydroxyl group, the protecting group may be eliminated, and then the compound may be subjected to the step of halogenation at the 6-position, and if the halogen-substituted compound has a protected hydroxyl group, the protecting group for the hydroxyl group may be eliminated, and then the compound may be subjected to the step of amination at the 6-position.

That is, in the case of the derivative wherein Y' is a hydrogen atom and B is 6-hydroxypurine, an amino group is introduced into this derivative if necessary via the step of halogenation at the 6-position, while in the case of the derivative wherein X' is neither a hydrogen atom nor a fluorine atom but a hydroxyl group (protected or not protected), the derivative is subjected as necessary to the step of dehydroxylation, or the step of dehydroxylation-fluorination at the β-position, for the hydroxyl group (X'), whereby ddA, FddA and their related compounds can be produced. The order for conducting these steps is not particularly limited to the order described and can be suitably selected.

Now, whole contents of Japanese Application No. 311918/1998, based on which the priority is claimed for this application, is incorporated by references in the specification of this application, if necessary.

EXAMPLES

Hereinafter, the present invention is described in more detail by reference to the Reference Examples and Examples.

Reference Example 1

Synthesis of 5'-O-trityl-3'-O-phenoxythiocarbonyl-2'-deoxy-adenosine from 5'-O-trityl-2'-deoxy-adenosine 0.50 g of 5'-O-trityl-2'-deoxy-adenosine was dissolved in 10.1 ml dry acetonitrile, and 373.9 mg (3 equivalents) of DMAP was added thereto. This solution was cooled to 0° C., and 0.28 ml (2 equivalents) of phenoxythiocarbonyl chloride was added slowly. This reaction solution was raised to room temperature and stirred as such for 3 hours, and 62.3 mg DMAP and 70.0 μl phenoxythiocarbonyl chloride were further added thereto. This reaction solution was stirred at room temperature for 2 days, and then 1.0 ml methanol was added to stop the reaction. This reaction solution was stirred for 30 minutes, and 30 ml methylene chloride and 15 ml aqueous saturated sodium hydrogen carbonate were added thereto, and the mixture was stirred vigorously. The separated organic layer was washed with 10 ml saturated saline, dried over sodium sulfate and concentrated. The resulting oily residue was purified with silica gel column chromatography (eluent: hexane/ethyl acetate) whereby 144.1 mg of the object compound (yield: 17.9%) was obtained.

Example 1

Synthesis of 5'-O-trityl-2',3'-dideoxy-adenosine from 5'-O-trityl-3'-O-phenoxythiocarbonyl-2'-deoxy-adenosine

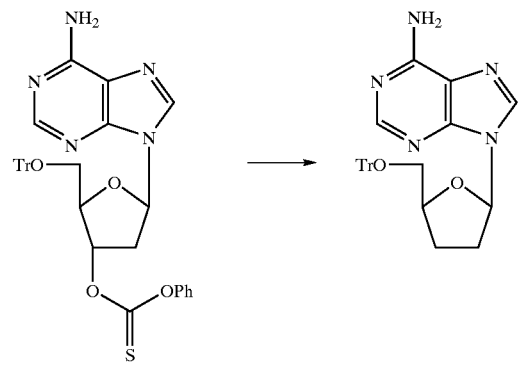

144.1 mg of 5'-O-trityl-3'-O-phenoxythiocarbonyl-2'-deoxy-adenosine was dissolved in 2.29 ml dimethoxyethane, and 0.18 ml triethylamine (5.5 equivalents) and 0.12 ml of 50% aqueous hypophosphorous acid ($H_3PO_2$; 5.0 equivalents) were added thereto. 1.0 mg of 2,2'-azobisisobutyronitrile (AIBN) was added to this solution and heated under reflux at 90° C. for 1 hour, and further 1.0 mg AIBN was added thereto, and the mixture was heated under reflux at 90° C. for 1 hour. This reaction solution was left at room temperature overnight, and further 3.0 mg AIBN was added thereto, and the mixture was heated under reflux at 90° C. for 6 hours. When the reaction was confirmed by high performance liquid chromatography (HPLC), it was found that the objective compound was formed in an area ratio of 2%.

Reference Example 2

Synthesis of 5'-O-trityl-3'-O-methylthiothiocarbonyl-2'-deoxy-adenosine from 5'-O-trityl-2'-deoxy-adenosine 1.0 g of 5'-O-trityl-2'-deoxy-adenosine was dissolved in 4.0 ml DMSO, and 0.24 ml (2 equivalents) of carbon disulfide was added thereto. This solution was cooled to 15° C., and 0.45 ml (1.1 equivalents) of 5 N aqueous sodium hydroxide was added slowly. This reaction solution was stirred at 15° C. for 30 minutes, and 0.14 ml (1.1 equivalents) of methyl iodide was added slowly. This reaction solution was stirred at 15° C. for 1.5 hours and added dropwise to 35 ml separately prepared water to stop the reaction. This reaction solution was stirred at room temperature for 20 minutes, and the resulting crystals were filtered and washed with 15 ml water and 20 ml hexane. The crystals were air-dried overnight and dried at 40° C. under reduced pressure to give 1.14 g (yield: 96.4%) of the title objective compound.

Example 2

Synthesis of 5'-O-trityl-2',3'-dideoxy-adenosine from 5'-O-trityl-3'-O-methylthiothiocarbonyl-2'-deoxy-adenosine

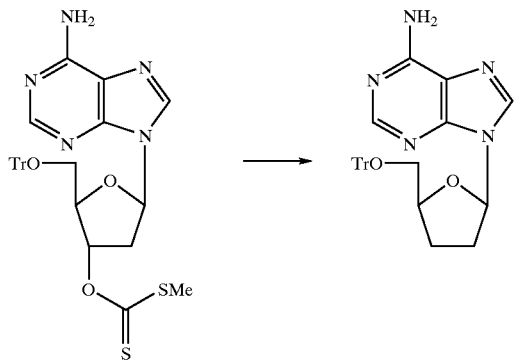

1.14 g of 5'-O-trityl-3'-O-methylthiothiocarbonyl-2'-deoxy-adenosine was dissolved in 5.0 ml dimethoxyethane, and 2.85 ml triethylamine (10 equivalents) and 1.05 ml of 50% aqueous hypophosphorous acid (5 equivalents) were added thereto. This solution was heated to 70° C., and 66.5 mg (0.2 equivalent) of AIBN dissolved in 4.0 ml dimethoxyethane was added thereto. After 1.5 hours, 33.3 mg (0.1 equivalent) of AIBN was further added thereto and heated under reflux for 1 hour. This reaction solution was cooled to room temperature and added dropwise to a separately prepared mixture of 50 ml methylene chloride and 30 ml saturated saline to stop the reaction. The organic layer was separated, dried over magnesium sulfate and concentrated. The resulting oily residue was recrystallized from toluene and the first crystals and the second crystals were combined to give the title objective compound in 56.1% yield.

Reference Example 3

Synthesis of 6-chloro-9-(5-O-trityl-3-O-benzoyl-2-deoxy-2-fluoro-β-D-arabinofuranosyl)-9H-purine 5'-O-trityl-3'-O-benzoyl-6-chlorpurine riboside (4.76 g, 7.5 mmol) was dissolved in 100 ml dry methylene chloride, and 3.6 ml (44.5 mmol) of pyridine was added thereto. After the mixture was cooled on ice, diethylaminosulfur trifluoride (DAST, 2.25 ml, 17 mmol) was added dropwise thereto under stirring, allowed to reach room temperature and further heated under reflux for 5 hours. After cooling, the reaction solution was added dropwise to 500 ml of 5% aqueous sodium hydrogen carbonate under vigorous stirring and stirred for 20 minutes. It was transferred to a separating funnel and shaken well, and the organic layer was recovered. The aqueous layer was washed with 100 ml chloroform. The organic layers were combined, washed with 200 ml water, dried over magnesium sulfate and filtered, and the solvent was distilled off. The residues were subjected to azeotropic distillation with toluene until the smell of pyridine disappeared, and then the reaction solution was dissolved in 50 ml benzene, subjected to a silica gel column (3.5×50 cm) and eluted with 0 to 12.5% ethyl acetate/benzene solution (4000 ml). Product fractions were collected and the solvent was distilled off whereby caramel was obtained. Yield, 3.80 g (FW: 635.1, 5.99 mmol, 80%).

$^1$H-NMR (CDCl$_3$) δ: 8.76 (1H, s, H2), 8.36 (1H, d, J=3.0 Hz, H8), 7.2–8.1 (ca 20H, Bz, Tr), 6.66 (1H, dd, J=21.7, J=2.7 Hz, H1'), 5.70 (1H, dd, J=17.0, J=3.0 Hz, H3'), 5.28 (1H, ddd, J=50.0, J=3.0, J=0.8 Hz, H2'), 4.42 (1H, m, H4'), 3.62 (1H, dd, J=10.4, J=5.2 Hz, H5' a), 3.54 (1H, dd, J=10.4, J=4.1 Hz, H5' b).

Synthesis of 9-(5-O-trityl-2-deoxy-2-fluoro-β-D-arabinofuranosyl) adenine

6-Chloro-9-(5-O-trityl-3-O-benzoyl-2-deoxy-2-fluoro-β-D-arabinofuranosyl)-9-H-purine (3.15 g, 4.98 mmol) was dissolved in 100 ml methanolic ammonia (saturated at 0° C.) and left in a sealed tube at 100° C. for 2 days. After cooling, the solvent was carefully distilled off, and the residues were dissolved in 100 ml chloroform. The insolubles were filtered off and the solution was applied to a silica gel column (3.5×50 cm) and eluted with 3 to 10% ethanol/methylene chloride solution (4000 ml). Product fractions were collected, and the solution was concentrated to give white crystals (1.87 g, 3.66 mmol, 73%)

Melting point: 210.5–212.5° C.

Synthesis of 9-(5-O-trityl-3-O-methylthiothiocarbonyl-2-deoxy-2-fluoro-β-D-arabinofuranosyl) adenine from 9-(5-O-trityl-2-deoxy-2-fluoro-β-D-arabinofuranosyl) adenine 246.3 mg (purity: 95.2%) of 9-(5-O-trityl-2-deoxy-2-fluoro-β-D-arabinofuranosyl) adenine was dissolved in 0.91 ml DMSO, and 0.055 ml (2 equivalents) of carbon disulfide was added thereto. This solution was cooled to 15° C., and 0.1 ml (1.1 equivalents) of 5 N aqueous sodium hydroxide was added slowly. This reaction solution was stirred at 15° C. for 30 minutes, and 0.032 ml (1.1 equivalents) of methyl iodide was added slowly. This reaction solution was stirred at 15° C. for 1.3 hours, and further 0.03 ml carbon disulfide and 0.1 ml of 5 N aqueous sodium hydroxide were added slowly. This reaction solution was stirred at 15° C. for 30 minutes, and 0.03 ml methyl iodide was added slowly. This reaction solution was stirred at 15 C. and added dropwise to 10 ml separately prepared water to stop the reaction. The resulting crystals were filtered, and the crystals were washed twice with 10 ml water and 10 ml hexane. The crystals were dried under reduced pressure at room temperature to give 250.9 mg (purity, 66.8%; yield, 60.8%) of the objective compound.

Example 3

Synthesis of 9-(2,3-dideoxy-2-fluoro-5-O-trityl-β-D-threo-pentofuranosyl) adenine from 9-(5-O-trityl-3-O-methylthiothiocarbonyl-2-deoxy-2-fluoro-β-D-arabinofuranosyl) adenine

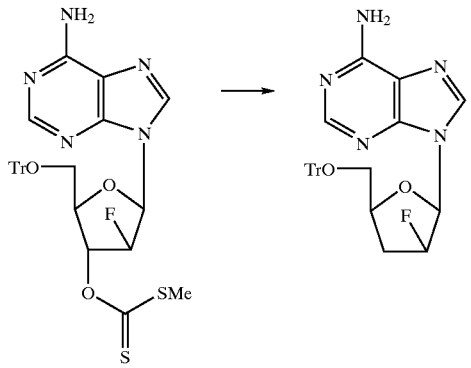

200 mg of 9-(5-O-trityl-3-O-methylthiothiocarbonyl-2-deoxy-2-fluoro-β-D-arabinofuranosyl) adenine was dissolved in 0.73 ml dimethoxyethane, and 0.42 ml triethylamine (13.6 equivalents) and 0.16 ml of 50% aqueous hypophosphorous acid (7 equivalents) were added thereto. This solution was heated until reflux, and 14.7 mg (0.4 equivalent) of AIBN dissolved in 0.44 ml dimethoxyethane was added thereto. After 5 hours, 14.7 mg (0.4 equivalent) of AIBN dissolved in 0.44 ml dimethoxyethane was further added thereto and heated under reflux 20 minutes. This reaction solution was cooled to room temperature, followed by adding 3 ml methylene chloride and 3 ml water dropwise to stop the reaction. The organic layer was separated and concentrated to give a solid substance which was then recrystallized from 3 ml toluene. The crystals were dried under reduced pressure to give the title objective compound in 70.2%.

Reference Example 4

Synthesis of 9-(5-O-trityl-3-O-methylthiothiocarbonyl-2-deoxy-2-fluoro-β-D-arabinofuranosyl) adenine from 9-(5-O-trityl-2-deoxy-2-fluoro-β-D-arabinofuranosyl) adenine 174.0 mg (purity: 86.5%) of 9-(5-O-trityl-2-deoxy-2-fluoro-β-D-arabinofuranosyl) adenine was dissolved in 1.2 ml DMSO and cooled to 13° C. 0.065 ml (1.1 equivalents) of 5 N aqueous sodium hydroxide and 0.072 ml (4 equivalents) of carbon disulfide were added thereto. This reaction solution was stirred at 13° C. for 15 minutes, and 0.036 ml (2 equivalents) of methyl iodide was added thereto. This reaction solution was added dropwise to 10 ml separately prepared water to stop the reaction. The resulting crystals were filtered, and the crystals were recrystallized from 3 ml acetonitrile and 4 ml water. The crystals were filtered, washed with water and dried at 45° C. under reduced pressure to give 127.9 mg (yield, 72.2%) of the title objective compound.

Synthesis of 9-(5-O-trityl-3-O-methylthiothiocarbonyl-2-deoxy-2-fluoro-β-D-arabinofuranosyl) adenine from 9-(5-O-trityl-2-deoxy-2-fluoro-β-D-arabinofuranosyl) adenine 4.80 g (purity: 86.5%) of 9-(5-O-trityl-2-deoxy-2-fluoro-β-D-arabinofuranosyl) adenine was dissolved in 33 ml DMSO and cooled to 12° C. 1.79 ml (1.1 equivalents) of 5 N aqueous sodium hydroxide and 1.94 ml (4 equivalents) of carbon disulfide were added slowly to this solution. Further, 1.01 ml (2 equivalents) of methyl iodide was further added slowly to this reaction solution. This reaction solution was stirred at 12° C. for 30 minutes and added dropwise to a separately prepared mixture of 50 ml water and 50 ml ethyl acetate to stop the reaction. The organic layer was separated and washed with 50 ml water, and this organic layer was concentrated to give an oily residue. This oily residue was recrystallized from 20 ml acetonitrile and filtered, and the crystals were dried at 45° C. under reduced pressure to give 3.95 g (purity, 98.0%; yield, 79.3%) of the objective compound.

Example 4

Synthesis of 9-(2,3-dideoxy-2-fluoro-5-O-trityl-β-D-threo-pentofuranosyl) adenine from 9-(5-O-trityl-3-O-methylthiothiocarbonyl-2-deoxy-2-fluoro-β-D-arabinofuranosyl) adenine—No. 2

102.13 mg of 9-(5-O-trityl-3-O-methylthiothiocarbonyl-2-deoxy-2-fluoro-β-D-arabinofuranosyl) adenine (purity: 98.0%) was dissolved in 0.83 ml dimethoxyethane, and 0.46 ml triethylamine (20 equivalents) and 0.172 ml of 50% aqueous hypophosphorous acid (10 equivalents) were added thereto. This solution was heated until reflux, and 16.4 mg (0.6 equivalent) of AIBN dissolved in 0.49 ml dimethoxyethane was added in 3 portions. This reaction solution was heated under reflux for 1 hour and 45 minutes and then cooled to room temperature, followed by adding 5 ml methylene chloride and 5 ml water dropwise to stop the reaction. The organic layer was separated and concentrated to give a solid substance which was then recrystallized from a mixture of 3.2 ml toluene and 3.2 ml methanol. The crystals were dried under reduced pressure to give the objective compound in 86.1%.

Example 5

Synthesis of 2',5'-di-O-acetyl-3'-deoxy-inosine from 9-(2,5-di-O-acetyl-3-bromo-3-deoxy-β-D-xylofuranosyl) hypoxanthine

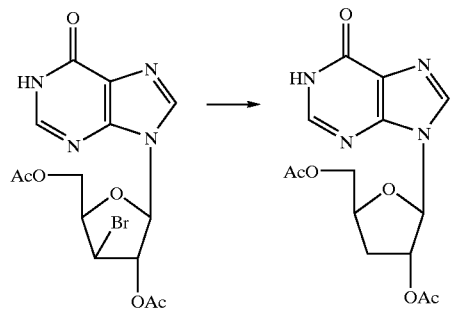

14.4 ml acetonitrile and 7.2 ml water were added to the solution of 24.98 g acetonitrile and 10.01 g of 9-(2,5-di-O-acetyl-3-bromo-3-deoxy-β-D-xylofuranosyl) hypoxanthine dissolved therein. A solution previously prepared by mixing 10.7 g triethylamine (4.4 equivalents) with 12.7 g of 50% aqueous hypophosphorous acid (4.0 equivalents) was added thereto. The pH value of this solution was decreased from 8.7 to 7.0 by adding 5 drops of 50% aqueous hypophosphorous acid. This solution was heated to 70° C., and 395.4 mg (0.1 equivalent) of AIBN dissolved in 3.0 ml acetonitrile was added thereto. This reaction solution was heated under reflux for 1 hour, then cooled to room temperature and neutralized to pH 7.0 with 25% aqueous sodium hydroxide. This reaction solution was concentrated, and 70 ml water was added to the residues which were then stirred at 60° C. for 1 hour and cooled to room temperature. The formed crystals were filtered and the crystals were washed with 25 ml water and 10 ml ethanol. The crystals were dried at 50° C. under reduced pressure to give 5.93 g (purity, 85.1%; yield, 62.2%) of the title object compound.

Example 6

Synthesis of 2',5'-di-O-acetyl-3'-deoxy-inosine from 9-(2,5-di-O-acetyl-3-bromo-3-deoxy-β-D-xylofuranosyl) hypoxanthine—No. 2

A solution previously prepared by dissolving 10.44 g sodium hypophosphite monohydrate (4.0 equivalents) in 11.2 ml water was added to the solution obtained by dissolving 10.23 g of 9-(2,5-di-O-acetyl-3-bromo-3-deoxy-β-D-xylofuranosyl) hypoxanthine in 37.24 g acetonitrile.

4 N aqueous sodium hydroxide was added to this solution whereby the pH value was raised from 5.8 to 7.0. This solution was heated to 70° C., and 404.6 mg (0.1 equivalent) of AIBN dissolved in 3.0 ml acetonitrile was added thereto. This reaction solution was stirred at 70° C. for 2 hours, then cooled to room temperature and neutralized to pH 7.0 with 4 N aqueous sodium hydroxide. This reaction solution was concentrated, and 50 ml water was added to the residues, stirred at 60° C. for 1 hour and then cooled to room temperature. The resulting crystals were filtered and the crystals were dried at 40° C. under reduced pressure whereby 4.89 g (purity, 82.6%; yield, 48.8%) of the title objective compound was obtained.

Example 7

Synthesis of 2',5'-di-O-acetyl-3'-deoxy-inosine from 9-(2,5-di-O-acetyl-3-bromo-3-deoxy-β-D-xylofuranosyl) hypoxanthine—No. 3

9.74 ml of 50% aqueous hypophosphorous acid (3.0 equivalents) was added to 63 ml water and cooled to 10° C., and 12.5 ml triethylamine (3.0 equivalents) was added thereto. The resulting solution was added to the solution of 31.38 g acetonitrile and 2.46 g of 9-(2,5-di-O-acetyl-3-bromo-3-deoxy-β-D-xylofuranosyl) hypoxanthine dissolved therein. 3.4 ml triethylamine was added to this solution whereby the pH value was raised from 4.3 to 8.0. This solution was heated to 60° C., and 811.7 mg (0.1 equivalent) of V-50 [2,2'-azobis(2-methylpropionamidine) dihydrochloride] dissolved in 5.0 ml water was added thereto. This reaction solution was stirred at 60° C. for 1 hour, neutralized to pH 4.5 with 4.0 ml of 25% aqueous sodium hydroxide, further stirred at 60° C. for 1 hour and then cooled to room temperature. The resulting crystals were filtered and the crystals were washed with 35 ml water. The crystals were dried at 55° C. under reduced pressure whereby 5.54 g (purity, 56.3%; yield, 54.9%) of the title objective compound was obtained.

Example 8

Synthesis of 2',5'-di-O-acetyl-3'-deoxy-inosine from 9-(2,5-di-O-acetyl-3-bromo-3-deoxy-β-D-xylofuranosyl) hypoxanthine—No. 4

A solution previously prepared by dissolving 15.43 g sodium hypophosphite monohydrate (2.0 equivalents) in 111 ml water was added to the solution of 74.03 g of acetonitrile and 30.06 g of 9-(2,5-di-O-acetyl-3-bromo-3-deoxy-O-β-xylofuranosyl) hypoxanthine dissolved therein. 25% aqueous sodium hydroxide was added to this solution to adjust the pH value to 8.5. This solution was heated to 55° C., and 1.96 g (0.1 equivalent) of V-50 [2,2'-azobis (2-methylpropionamidine) dihydrochloride] was added thereto. After this reaction solution was stirred at 60° C. for 1 hour, 111 ml water was added thereto, and the solution was further stirred at 60° C. for 1 hour. This reaction solution was neutralized to pH 7.0 with 25% aqueous sodium hydroxide. This reaction solution was further stirred at 60° C. for 1 hour, then cooled to 5° C. and stored overnight, followed by raising the temperature to 22° C. and stirring for 4 hours. The resulting crystals were filtered and the crystals were washed with 26 ml water and 10 ml ethanol. The crystals were dried at 55° C. under reduced pressure whereby the title objective compound was obtained with 72.8% purity in 50.0% yield.

Example 9

Synthesis of 2',5'-di-O-acetyl-3'-deoxy-inosine from 9-(2,5-di-O-acetyl-3-bromo-3-deoxy-β-D-xylofuranosyl) hypoxanthine—No. 5

19.8 g of 50% aqueous hypophosphorous acid (3.0 equivalents) was added to 104 ml water and cooled to 16° C., and 15.23 g triethylamine (3.0 equivalents) was added thereto. The resulting solution was added to the solution of 51.18 g acetonitrile and 20.76 g of 9-(2,5-di-O-acetyl-3-bromo-3-deoxy-β-D-xylofuranosyl) hypoxanthine dissolved therein. The temperature of this solution was raised to 43° C., and triethylamine was added to raise the pH value from 3.8 to 8.0. This solution was heated to 49° C., and 1.62 g (0.1 equivalent) of VA-044 [2,2'-azobis[2-(2-imidazoline-2-yl) propane] dihydrochloride] dissolved in 8.3 ml water was added thereto. This reaction solution was stirred at 50° C. for 30 minutes, neutralized to pH 4.0 with 3.54 g of 25% aqueous sodium hydroxide, further stirred at 50° C. for 1.5 hours and cooled to 10° C. This reaction solution was neutralized to pH 6.0 with 5.94 g of 25% aqueous sodium hydroxide. This reaction solution was stirred at 10° C. for 1.5 hours, and the resulting crystals were filtered and washed with 62 ml water. The title objective compound was obtained in 80.6% yield as determined by analysis of the crystals.

Example 10

Synthesis of 2',5'-di-O-acetyl-3'-deoxy-inosine from 9-(2,5-di-O-acetyl-3-bromo-3-deoxy-β-D-xylofuranosyl) hypoxanthine—No. 6

A solution previously prepared by dissolving 3.716 g sodium hypophosphite monohydrate ($NaH_2PO_2 \cdot H_2O$; 2.0 equivalents) in 33.4 ml water was added to the solution of 18.16 g acetonitrile and 7.21 g of 9-(2,5-di-O-acetyl-3-bromo-3-deoxy-β-D-xylofuranosyl) hypoxanthine dissolved therein. 1.8 ml of 25% aqueous sodium hydroxide was added to this solution to adjust the pH value to 8.5. This solution was heated to 60° C., and 560.8 mg (0.1 equivalent) of VA-044 [2,2'-azobis[2-(2-imidazoline-2-yl) propane] dihydrochloride] dissolved in 2.8 ml water was added thereto. While this reaction solution was kept at pH 4.0 by suitably adding 25% aqueous sodium hydroxide, the solution was stirred at 60° C. for 1 hour. This reaction solution was cooled to room temperature and neutralized to pH 6.2 with 25% aqueous sodium hydroxide. The resulting crystals were filtered and the crystals were washed with 17.6 ml water and 2 ml ethanol. The crystals were dried at 60° C. under reduced pressure whereby 5.089 g (purity:77.6%; yield: 67.6%) of the title objective compound was obtained.

Example 11

Synthesis of 2',5'-di-O-acetyl-3'-deoxy-inosine from 9-(2,5-di-O-acetyl-3-bromo-3-deoxy-β-D-xylofuranosyl) hypoxanthine—No. 7

A solution previously prepared by dissolving 1.06 g sodium hypophosphite monohydrate (2.0 equivalents) in 9.47 ml water was added to the solution of 11.27 g acetonitrile and 2.03 g of 9-(2,5-di-O-acetyl-3-bromo-3-deoxy-β-D-xylofuranosyl) hypoxanthine dissolved therein. 0.76 g of 25% aqueous sodium hydroxide was added to this solution and further 0.14 g (0.1 equivalent) of VA-086 [2,2'-azobis[2-methyl-N-(2-hydroxyethyl) propionamide]] dissolved in 1.4 ml water was added thereto. 0.12 g of 6 N hydrochloric acid was added to this reaction solution to adjust the pH value to 8.6. This reaction solution was stirred at 60° C. overnight and further stirred at 68° C. for 2 hours whereby the title objective compound was obtained in 1.2% yield as determined by HPLC analysis.

Example 12

Synthesis of 2',5'-di-O-acetyl-3'-deoxy-inosine from 9-(2,5-di-O-acetyl-3-bromo-3-deoxy-β-D-xylofuranosyl) hypoxanthine—No. 8

A solution previously prepared by dissolving 3.18 g sodium hypophosphite monohydrate (2.0 equivalents) in 28.6 ml water was added to the solution of 15.34 g acetonitrile and 6.23 g of 9-(2,5-di-O-acetyl-3-bromo-3-deoxy-β-D-xylofuranosyl) hypoxanthine dissolved therein. 1.49 g of 25% aqueous sodium hydroxide was added to this solution to adjust the pH value to 8.5. 0.58 g (0.1 equivalent) of VA-044B [2,2'-azobis[2-(2-imidazoline-2-yl) propane] disulfate] dissolved in 3.0 ml water was added to this solution. This reaction solution was adjusted to pH 8.5 by adding 0.59 g of 25% aqueous sodium hydroxide, and the reaction solution was stirred at 60° C. for 1 hour. This reaction solution was neutralized to pH 7.0 by adding 5.75 g of 25% aqueous sodium hydroxide and then cooled to room temperature. The resulting crystals were filtered and the crystals were washed with 16.5 ml water. The crystals were dried at 60° C. under reduced pressure whereby 3.87 g (purity, 58.1%; yield, 44.6%) of the title objective compound was obtained.

Reference Example 5

Synthesis of (-)-3'-5'-O-(1,1,3,3-tetraisopropyl-1,3-disiloxanediyl)-2'-O-imidazolylthiocarbonyl-adenosine from (-)-3',5'-O-(1,1,3,3-tetraisopropyl-1,3-disiloxanediyl) adenosine

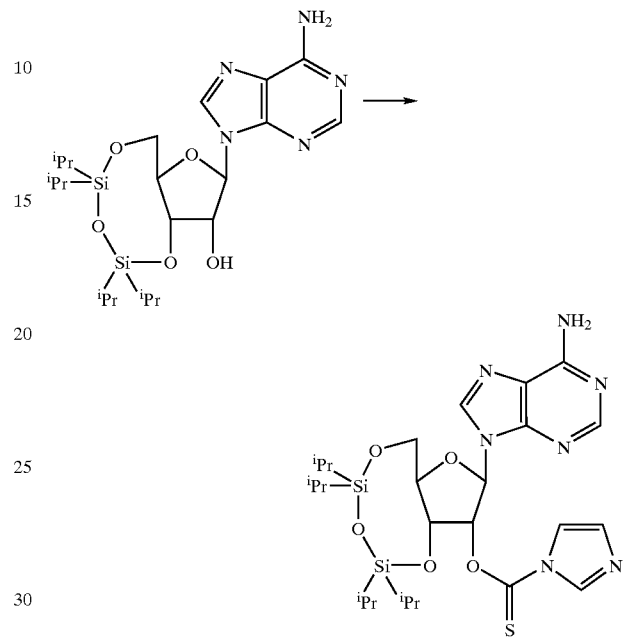

0.76 g of (-)-3',5'-O-(1,1,3,3-tetraisopropyl-1,3-disiloxanediyl) adenosine was dissolved in 15 ml dry dimethylformamide, and 0.74 g of 1,1'-thiocarbonyldiimidazole was added thereto. This reaction solution was stirred at room temperature overnight, followed by raising the temperature to 70° C. and stirring for 6 hours. 250 ml ethyl acetate and 50 ml water were added to this reaction solution to stop the reaction. The organic layer was separated, washed twice with 50 ml water, then dried over magnesium sulfate and concentrated. The resulting oily residue was purified by silica gel column chromatography (eluent: methanol/methylene chloride) to give 0.76 g (purity: 81.7%) of the objective compound.

Example 13

Synthesis of 2'-deoxyadenosine from (-)-3',5'-O-(1,1,3,3-tetraisopropyl-1,3-disiloxanediyl)-2'-O-imidazolylthiocarbonyl-adenosine

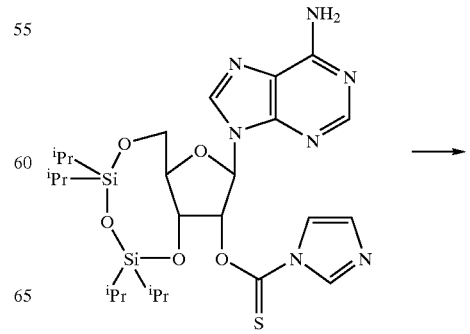

-continued

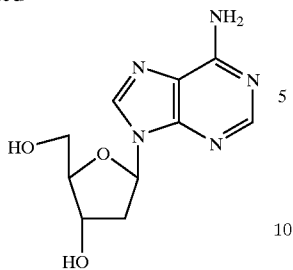

692 mg of, (-)-3',5'-O-(1,1,3,3-tetraisopropyl-1,3-disiloxanediyl)-2'-O-imidazolylthiocarbonyl-adenosine was dissolved in 4.6 ml dimethoxyethane and added to 0.86 ml triethylamine (5.5 equivalents) and 0.60 ml of 50% aqueous hypophosphorous acid (5.0 equivalents). After 18.3 mg AIBN was added to this solution, the mixture was heated under reflux at 100° C. for 30 minutes, and after 18.3 mg AIBN was further added to this solution, the mixture was heated under reflux at 100° C. for 30 minutes. This reaction solution was cooled to room temperature, and 20 ml ethyl acetate, 10 ml dimethoxy ethane and 10 ml water were added to stop the reaction. The organic layer was separated and concentrated to give an oily residue. This oily residue was dissolved in 5.0 ml tetrahydrofuran, and 2.0 ml of 1.0 M tetrabutyl ammonium fluoride in tetrahydrofuran was added thereto. This solution was stirred at 70° C. for 1 hour and cooled to room temperature. This reaction mixture was concentrated, and 30 ml water and 20 ml diethyl ether were added thereto, and the aqueous layer was washed twice with 20 ml diethyl ether. The title objective compound was obtained in 33% yield as determined by HPLC analysis.

Example 14

Synthesis of 9-(2,3-dideoxy-2-fluoro-5-O-trityl-β-D-threo-pentofuranosyl) adenine from 9-(5-O-trityl-3-O-methylthiothiocarbonyl-2-deoxy-2-fluoro-β-D-arabinofuranosyl) adenine—No. 3

60.2 mg of 9-(5-O-trityl-3-O-methylthiothiocarbonyl-2-deoxy-2-fluoro-β-D-arabinofuranosyl) adenine (purity: 98.0%) was dissolved in 1.0 ml dimethoxyethane, and 110 mg of dimethyl phosphite ((CH$_3$O)$_2$P(O)H; 10 equivalents) was added thereto. This solution was heated until reflux, and 10.0 mg (0.6 equivalent) of AIBN dissolved in 0.6 ml dimethoxyethane was added in 3 portions.

This reaction solution was heated under reflux for 2 hours and then cooled to room temperature. The solution was concentrated under reduced pressure to give the objective compound in yield 84.1% as determined by HPLC analysis.

The reaction was conducted in the same manner as above in Example 14, except using 138 mg of diethyl phosphite (10 equivalents) in place of the 110 mg of dimethyl phosphite (10 equivalents). Thus obtained reaction solution was cooled to room temperature, and the solution was concentrated under reduced pressure to give the objective compound in yield 82.2% as determined by HPLC analysis.

Effects of the Invention

According to the present invention, sugar-moiety hydroxyl groups and halogen atoms in nucleic acid derivatives (including nucleic acids or derivatives thereof and nucleic acid-related compounds) can be radically reduced with any one of hypophosphorous acids which may be in the salts thereof, and phosphites (esters), so this process can be utilized to provide an industrially useful and highly safe process for producing the reduced compounds at low costs.

What is claimed is:

1. A process for producing a nucleoside derivative represented by the formula (II):

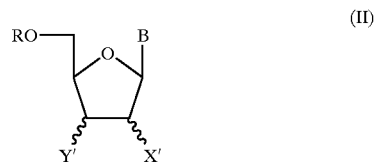

wherein B represents a nucleic acid base residue or a derivative thereof, R represents a hydrogen atom or a hydroxy group-protecting group, and one of Y' and X' represents a hydrogen atom and the other represents a hydrogen atom, a fluorine atom, a hydroxyl group or a protected hydroxyl group, respectively, which comprises allowing a nucleoside derivative represented by the formula (I):

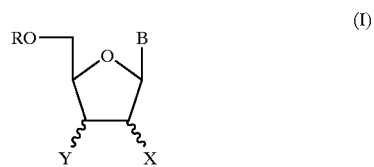

wherein B and R have the same meanings as defined above, and one of Y and X represents a leaving group and the other represents a hydrogen atom, a fluorine atom, a hydroxyl group or a protected hydroxyl group, respectively, to react with at least one compound selected from hypophosphorous acids, or salts thereof and esters of phosphorous acid in the presence of a radical reaction initiator.

2. The process according to claim 1, wherein B is a purine base or a pyrimidine base, or a derivative thereof.

3. The process according to claim 2, wherein B is any base of hypoxanthine, adenine, guanine, uracil, thymine and cytosine or a derivative thereof.

4. The process according to claim 1, wherein R is selected from the group consisting of a hydrogen atom, an acyl group, an alkyl group, an aralkyl group and a silyl group.

5. The process according to claim 4, wherein the acyl group is an acetyl group or a benzoyl group, and the aralkyl group is a trityl group.

6. The process according to claim 1, wherein said leaving group represented by either Y or X is selected from the group consisting of halogen atoms and O-thiocarbonyl residues, provided that said leaving group is not a fluorine atom.

7. The process according to claim 1, wherein the protected hydroxyl group in the case where either Y or X represents a protected hydroxyl group is selected from the group consisting of an acyloxy group, an alkyloxy group, an aralkyloxy group and a silyloxy group.

8. The process according to claim 7, wherein the acyloxy group is an acetyloxy group or a benzoyloxy group.

9. The process according to claim 1, wherein hypophosphorous acid is in the form of a sodium salt.

10. The process according to claim 1, wherein the radical reaction initiator is an azo compound.

11. The process according to claim 6, wherein the O-thiocarbonyl is selected from the group consisting of O-phenoxythiocarbonyl, O-parafluorophenoxythiocarbonyl, O-methylthiothiocarbonyl, O-phenyithiothiocarbonyl and O-imidazolylthiocarbonyl.

12. The process according to claim 1, wherein in the general formula (II), B is an adenine, Y' is a hydrogen atom, X' is a hydrogen atom or a fluorine atom, R is a hydrogen atom or a hydroxy group-protecting group, and if R is the protecting group, this group is further eliminated to produce ddA or FddA.

13. The process according to claim 1, wherein the compound produced in claim 1 in which B is a purine base or a derivative thereof, Y' is a hydrogen atom, X' is a hydroxyl group or a protected hydroxyl group, is subjected to at least one step of the step of deprotecting the hydroxyl group, the step of halogenation at the 6-position, the step of amination at the 6-position and the step of fluorination at the 2'-position to produce FddA.

14. The process according to claim 13, wherein said produced compound in which B is an adenine, Y' is a hydrogen atom, X' is a hydroxyl group or a protected hydroxyl group, is subjected to the step of fluorination at the 2'-position, and if R is the protecting group, the compound is further subjected to the step of deprotection.

15. The process according to claim 13, wherein said produced compound in which B is 6-halogenopurine, Y' is a hydrogen atom, and X' is a hydroxyl group or a protected hydroxyl group, is subjected to the step of fluorination at the 2'-position and the step of amination at the 6'-position in this order or in the reverse order, and if R is the protecting group, the compound is further subjected to the step of deprotection.

16. The process according to claim 13, wherein said produced compound in which B is 6-hydroxypurine, Y' is a hydrogen atom, and X' is a hydroxyl group or a protected hydroxyl group, is subjected to the step of halogenation at the 6-position to produce the compound substituted with a halogen at the 6-position which is then subjected to the step of fluorination at the 2'-position and the step of amination at the 6-position in this order or in the reverse order, and if R is the protecting group, the compound is further subjected to the step of deprotection, provided that if said compound has a protected hydroxyl group, its protecting group is optionally eliminated and then the compound is optionally subjected to the step of halogenation at the 6-position, and if said halogen-substituted compound has a protected hydroxyl group, the protecting group for said hydroxyl group is optionally eliminated and then the compound is optionally subjected to the step of amination at the 6-position.

17. The process of claim 1, wherein B is selected from the group consisting of uracil, thymine, cytosine, hypoxanthine, adenine, and guanine.

18. The process of claim 1, wherein said leaving group is selected from the group consisting of chlorine atom, bromine atom, iodine atom, and O-thiocarbonyl residues represented by the formula (III):

(III)

wherein, Z represents any one of H, NR'R", OR' and SR'; and wherein R' and R" independently of each other are selected from the group consisting of phenyl, tolyl, naphthyl, $C_1$–$C_5$ alkyl, benzyl, phenethyl, $C_1$–$C_5$ alkyloxy, methylamino, ethylamino, dimethylamino, each of which may be substituted, and R' and R" may be combined to form a $C_1$–$C_5$ cyclic group.

19. The process of claim 1, wherein said radical reaction initiator is selected from the group consisting of 2,2'-azobis (2-methylpropionamidine) dihydrochloride; 2,2'-azobis [2-(2-imidazoline-2-yl) propane] dihydrochloride; 2,2'-azobis [2-(2-imidazoline-2-yl) propane] disulfate; 2,2'-azobis [2-(2-imidazoline-2-yl) propane; 2,2'-azobis [2-methyl-N-(2-hydroxyethyl) propionamide; and azodi-t-octane.

20. The process of claim 19, wherein B is selected from the group consisting of uracil, thymine, cytosine, hypoxanthine, adenine, and guanine.

* * * * *